United States Patent
Liu et al.

(10) Patent No.: US 10,028,678 B2
(45) Date of Patent: Jul. 24, 2018

(54) DEVICE AND METHOD FOR MEASURING CERVICAL VERTEBRA MOVEMENT

(71) Applicant: BOE TECHNOLOGY GROUP CO., LTD., Beijing (CN)

(72) Inventors: Lang Liu, Beijing (CN); Xuewen Lv, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 10 days.

(21) Appl. No.: 15/037,638

(22) PCT Filed: Nov. 16, 2015

(86) PCT No.: PCT/CN2015/094726
§ 371 (c)(1),
(2) Date: May 18, 2016

(87) PCT Pub. No.: WO2016/188054
PCT Pub. Date: Dec. 1, 2016

(65) Prior Publication Data
US 2017/0105661 A1    Apr. 20, 2017

(30) Foreign Application Priority Data
May 23, 2015 (CN) .......................... 2015 1 0267371

(51) Int. Cl.
*A61B 5/00*     (2006.01)
*A61B 5/11*     (2006.01)
*A61B 90/00*    (2016.01)

(52) U.S. Cl.
CPC .......... *A61B 5/1121* (2013.01); *A61B 5/4566* (2013.01); *A61B 90/06* (2016.02); *A61B 2090/067* (2016.02)

(58) Field of Classification Search
CPC ................................ A61B 5/1121; A61B 5/11
See application file for complete search history.

(56) References Cited

U.S. PATENT DOCUMENTS 5,744,953 A * 4/1998 Hansen ................ A61B 5/1036
                                                    324/207.17
2007/0241271 A1* 10/2007 Chin .................. G01D 5/34746
                                                    250/231.13
(Continued)

FOREIGN PATENT DOCUMENTS

CN        1290512 A      4/2001
CN      201131742 Y     10/2008
(Continued)

OTHER PUBLICATIONS

Written Opinion of the International Searching Authority from corresponding PCT Application No. PCT/CN2015/094726 (5 pages).

*Primary Examiner* — Michael C Strout
*Assistant Examiner* — Nicholas E Kolderman
(74) *Attorney, Agent, or Firm* — Harness, Dickey & Pierce, P.L.C.

(57) ABSTRACT

The present disclosure provides device and method for measuring cervical vertebra movement. The device comprises a sensor unit, a computation unit, a storage unit and a determination unit. The sensor unit comprises at least one transmission part and at least one reception part. Either of the transmission part and the reception part moves along with user's head, the other fixes relative to user's body. The transmission part transmits detection signals and the reception part receives them. The computation unit computes, based on detection signals, distance changes in a distance between the transmitting and reception part before and after user's head moves. The storage unit stores a mapping table indicating relations between distance changes and movement angles of user's head. The determination unit inquires the mapping table based on distance changes to determine (Continued)

movement angles of user's head. The device is simple, easily operated and practicable.

14 Claims, 5 Drawing Sheets

(56) References Cited

U.S. PATENT DOCUMENTS

| | | | |
|---|---|---|---|
| 2009/0322763 A1* | 12/2009 | Bang | G06F 3/011 345/474 |
| 2011/0004082 A1* | 1/2011 | Poeze | A61B 5/14532 600/323 |
| 2012/0086801 A1* | 4/2012 | Larsen | G02B 27/0093 348/135 |
| 2013/0274587 A1* | 10/2013 | Coza | A61B 5/6804 600/409 |
| 2014/0081180 A1 | 3/2014 | Ghajar | |
| 2015/0323388 A1* | 11/2015 | Kostic | A61G 13/10 250/338.1 |

FOREIGN PATENT DOCUMENTS

| | | |
|---|---|---|
| CN | 104382599 A | 3/2015 |
| CN | 104825168 A | 8/2015 |
| CN | 204839517 U | 12/2015 |
| JP | 2011-120683 A | 6/2011 |

\* cited by examiner

DEVICE AND METHOD FOR MEASURING CERVICAL VERTEBRA MOVEMENT

This application claims the benefit and priority of Chinese Patent Application No. 201510267371.0 filed May 23, 2015. The entire disclosure of the above application is incorporated herein by reference.

FIELD

The present disclosure relates to the technical field of medical instruments, particularly, a device and a method for measuring cervical vertebra movement.

BACKGROUND

Currently, with increasing awareness of health, people are more and more aware of harms caused by cervical vertebra problems. In order to determine health conditions of a cervical vertebra, an accurate measurement needs to be made on the cervical vertebra movements. The cervical vertebra movements are quite complex, including head-up, head-down, head flat turn from left/right to right/left (eyes look straight ahead, head turns, and eyes keep a unchanged vertical distance from the ground), and head rotation from left/right to right/left (eyes look straight ahead, head turns, and the vertical distance between eyes and the ground changes), and so forth. In the prior art, an angular velocity sensor can be used to measure the cervical vertebra movements. Usually, the angular velocity sensor makes measurements within a cycle of the cervical vertebra movements. Specifically, the angular velocity sensor measures a range of the cervical vertebra movements, and then the range is averaged to compute an average angle offset. As the angular velocity sensor measures an average value for the cervical vertebra movements, a real time angle monitoring on the user cannot be achieved. In addition, when an angular velocity sensor is used for measurement, a beginning point and an ending point for the cervical vertebra movements need to be determined. A beginning state where the cervical vertebra of the user is not upright will lead to a measurement error, thus decreasing measurement accuracy.

SUMMARY

The embodiments of the disclosure provide a device and a method for measuring cervical vertebra movement.

According to one aspect, the disclosure provides a device for measuring cervical vertebra movement, comprising a sensor unit, a computation unit, a storage unit and a determination unit. The sensor unit may comprise at least one transmission part and at least one reception part. Either of the transmission part and the reception part is arranged to move along with the head of a user, and the other one is fixed relative to the body of the user. The transmission part may be configured to transmit a detection signal, the reception part may be configured to receive the detection signal transmitted by the transmission part. The computation unit may be configured to compute, based on the detection signal received by the reception part, a distance change in a distance between the transmission part and the reception part before and after the head of the user moves. The storage unit may be configured to store a mapping table indicating a relation between the distance change and a movement angle of the head of the user. The determination unit may be configured to inquire the mapping table based on the distance change to determine the movement angle of the head of the user.

In the embodiments of the disclosure, the transmission part may have at least one transmission terminal and the reception part may have at least one reception terminal. The transmission terminal may be configured to transmit the detection signal and the reception terminal may be configured to receive the detection signal transmitted by the corresponding transmission terminal.

In the embodiments of the disclosure, the computation unit may be configured to compute a distance change in a distance between each transmission terminal and each corresponding reception terminal before and after the head of the user moves.

In the embodiments of the disclosure, each transmission terminal transmits a different detection signal.

In the embodiments of the disclosure, an angle between a connection line connecting the transmission part with the corresponding reception part and a reference axis is not equal to zero, wherein the reference axis is a central axis of the body of the user in a vertical direction when the user stands upright and looks straight ahead.

In the embodiments of the disclosure, the transmission part may include one transmission terminal, and the reception part may include a plurality of reception terminals. In this case, the computation unit may be configured to compute a distance change in a distance between the transmission terminal and each of the plurality of reception terminals before and after the head of the user moves, In the embodiments of the disclosure, the transmission part may include a plurality of transmission terminals, the reception part may include one reception terminal. In this case the computation unit may be configured to compute a distance change in a distance between each of the plurality of transmission terminals and the reception terminal before and after the head of the user moves.

In the embodiments of the disclosure, the device for measuring cervical vertebra movement may further comprise a movement pattern determination unit configured to determine a movement pattern for the head of the user based on the distance change and a pre-established relation between the distance change and the movement pattern for the head of the user.

In the embodiments of the disclosure, the transmission part may be an infrared transmitter and the reception part may be an infrared receiver.

In the embodiments of the disclosure, the detection signal may be an infrared ray with a wavelength of 5.6~15 μm.

In the embodiments of the disclosure, the transmission part and the reception part may be cylindrical in shape.

In the embodiments of the disclosure, each of the transmission part and the reception part may have a length of 2~3 cm.

In the embodiments of the disclosure, the transmission part may periodically transmit the detection signal at an interval of T2, wherein a duration for transmitting the detection signal is T1, T2=KT1, wherein K is an integer which is greater than or equal to 1.

According to the other aspect, the disclosure provides a method for measuring cervical vertebra movement, comprising: computing, in response to at least one reception part receiving a detection signal transmitted by at least one transmission part, a distance change in a distance between each transmission part and corresponding reception part before and after the head of the user moves, and determining a movement angle of the head of the user based on the distance change and a pre-established relation between the distance change and the movement angle of the head of the user, wherein either of the transmission part and the reception part is arranged to move along with the head of the user, and the other one is fixed relative to the body of the user.

In the embodiments of the disclosure, the transmission part may have at least one transmission terminal, the reception part may have at least one reception terminal. The transmission terminal may be configured to transmit the detection signal, and the reception terminal may be configured to receive the detection signal transmitted by the transmission terminal. The step of computing the distance change may comprise computing the distance change in the distance between each transmission terminal and each corresponding reception terminal before and after the head of the user moves are computed.

In the embodiments of the disclosure, the method for measuring cervical vertebra movement may further comprise determining a movement pattern for the head of the user based on the distance change and a pre-established relation between the distance change and the movement pattern for the head of the user.

The device for measuring cervical vertebra movement according to embodiments of the disclosure is simple in structure, easily operated and highly practicable. Accordingly, the method for measuring cervical vertebra movement according to embodiments of the disclosure is simple and easy to be achieved.

DRAWINGS

In order to illustrate the technical solutions of the embodiments of the disclosure more clearly, a brief introduction to figures of the embodiments is made as follows. It should be known that figures described below merely relate to some embodiments of the disclosure, but do not limit the disclosure, wherein, FIG. 1 is a schematic diagram illustrating a device for measuring cervical vertebra movement and a use thereof according to a first embodiment of the disclosure.

DETAILED DESCRIPTION

In order to make problems to be solved, technical solutions and advantages of the embodiments of the disclosure clearer, a clear and complete description to the technical solutions of the embodiments of the disclosure shall be made in combination with figures of the embodiments of the disclosure. The embodiments to be described below are only some of embodiments, but not all the embodiments. Based on the described embodiments of the disclosure, those skilled in the art may obtain some other embodiments without creative work, but all the other embodiments shall fall within the protection scope of the disclosure.

Figure 1:
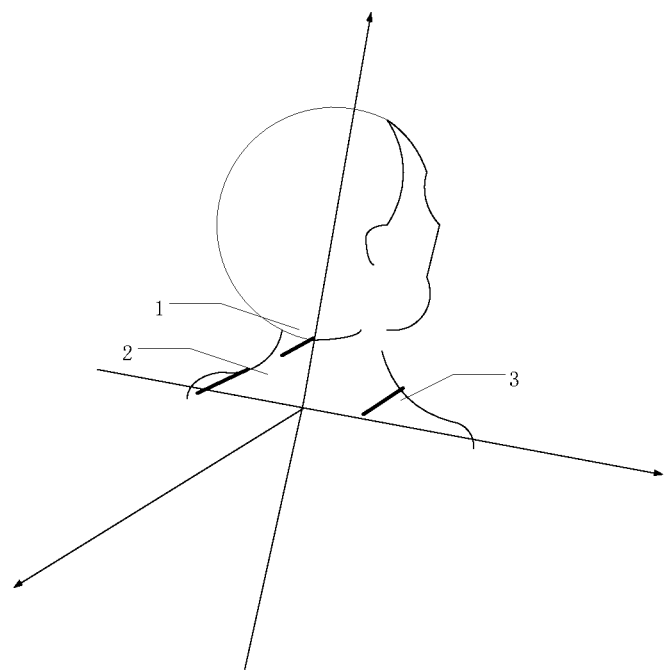

FIG. 1 is a schematic diagram illustrating a device for measuring cervical vertebra movement and a use thereof according to a first embodiment of the disclosure. As shown by FIG. 1, the device according the embodiment may comprise a sensor unit, a computation unit, a storage unit and a determination unit. The sensor unit may comprise at least one transmission part (one transmission part 1 in the embodiment) and at least one reception part (two reception parts 2 and 3 in the embodiment). The transmission part 1 may transmit a detection signal (e.g., a detection wave). The reception parts 2 and 3 may receive the detection signal transmitted by the transmission part 1. Either of the transmission part and the reception part is configured to move along with the head of a user, and the other one is fixed relative to the body of the user.

For example, the transmission part (or the reception part) may be schematically arranged at the skull to move along with the head of a user. Thus, the transmission part or the reception part may move along with the head to indicate a movement of the cervical vertebra. For example, the reception part (or the transmission part) may be schematically arranged at any of the first to the seventh centrums of the human body to be fixed relative to the body of the user. In this case, in consideration of the detection effect, the reception part (or the transmission part) may be arranged at any of the third to the fifth centrums of the human body. Thus, either of the transmission part and the reception part is stationary relative to the head of the user, and the other one is moving relative to the head of the user, which can ensure measurement accuracy.

The computation unit may compute (i.e., with a processor), based on the detection signal received by the reception part, a distance change in a distance between the transmission part and the reception part before and after the head of the user moves. For example, the detection signal may be an infrared signal, a laser signal and so forth. In this case, the distance between the transmission part and the reception part may be computed with an infrared distance measurement method or a laser distance measurement method. For example, the detection signal may also be a magnetic field signal. In this case, the distance between the transmission part and the reception part may be computed by a magnetic field distance measurement method based on a magnetic field intensity of a magnetic dipole at any point in the space. When the distance is computed, parameters of the detection signal may be used, such as, a wavelength or a frequency of the detection signal, a time from transmission to reception of the detection signal, an energy transmitted by the detection signal, or any other parameters for computing the distance. Details of the specific distance measurement principle will not be described.

The storage unit may store (i.e., in memory) a mapping table indicating a relation between the distance change and a movement angle of the head of the user, for example, there may be a plurality of mapping tables for different head movement patterns.

The determination unit may inquire (i.e., with a processor) the mapping table based on the distance change to determine the movement angle of the head of the user.

Figure 2:
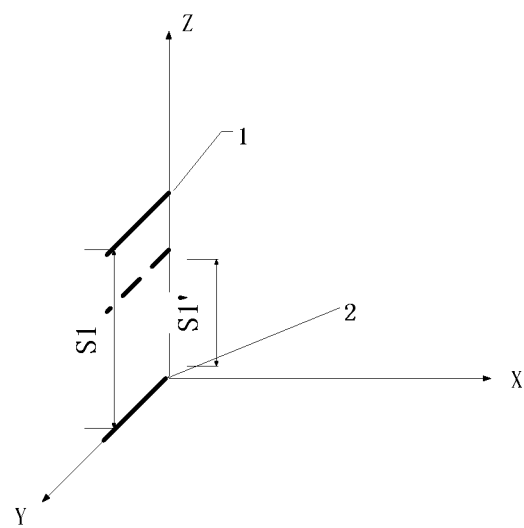
FIG. 2 is a schematic diagram illustrating a device for measuring cervical vertebra movement and its measurement on the user's head-up and head-down according to a second embodiment of the disclosure.

FIG. 2 is a schematic diagram illustrating a device for measuring cervical vertebra movement and its measurement on the user's head-up and head-down according to a second embodiment of the disclosure. As shown by FIG. 2, in the device for measuring cervical vertebra movement according to the embodiment, the sensor unit comprises one transmission part 1 and one reception part 2. The transmission part 1 has one transmission terminal and the reception part 2 has one reception terminal. In this case, the computation unit is configured to compute a distance change in a distance between the transmission terminal and the reception terminal before and after the head of the user moves.

As stated above, movement patterns for the cervical vertebra of a person may include head-up, head-down, head flat turn from left/right to right/left, and head rotation from left/right to right/left, and so forth. A detailed description to a process for the device for measuring cervical vertebra movement according to the embodiments of present disclosure to make measurements on these movements of the head of the user will be made as follows. In the following description, suppose the transmission part 1 is arranged to move along with the head of a user, and the reception part 2 is configured to be fixed relative to the body of the user.

As shown by FIG. 2, a virtual coordinate system is established at the positions where the transmission part 1 and the reception part 2 are. A process for the device for measuring cervical vertebra movement to make measurements on head-up and head-down is first described below. When the cervical vertebra of the user does not move, namely, the head of the user maintains at a fixed position, a distance between the transmission terminal of the transmission part 1 and the reception terminal of the reception part 2 of the sensor unit is also fixed, and is recorded as S1. Once the head of the user moves, the distance from the transmission terminal of the transmission part 1 to the reception terminal of the reception part 2 of the sensor unit varies. Specifically, when the user heads up, the transmission part 1 moves downward relative to its initial state, at this time, a direct distance from the transmission terminal of the transmission part 1 to the reception terminal of the reception part 2 decreases. When the user heads down, the transmission part 1 moves upward relative to its initial state, at this time, the distance from the transmission terminal of the transmission part 1 to the reception terminal of the reception part 2 increases. Then, based on the parameters of the detection signals received by the reception part 2, the computation unit may obtain a distance S1' from the transmission terminal to the reception terminal, and further compute a distance change S1–S1' in a distance between the transmission terminal of the transmission part 1 and the reception terminal of the reception part 2 before and after the head of the user moves. The storage unit is pre-stored with a mapping table indicating relation between the distance change in a distance, between the transmission terminal of the transmission part and the reception terminal of the reception part, and the movement angle of the head of the user. Lastly, the determination unit may find the movement angle of the head of the user based on data in the mapping table.

In this embodiment, a process for the device for measuring cervical vertebra movement to make measurements on angles for head flat turn from left/right to right/left is substantially the same with the process for the device for measuring cervical vertebra movement to make measurements on angles for head-up and head-down, and the difference only lies in when determining movement angles of the head of the user, the determination unit inquires a mapping table corresponding to head flat turn from left/right to right/left in the storage unit based on the distance changes to determine angles for head flat turn from left/right to right/left.

In this embodiment, a process for the device for measuring cervical vertebra movement to make measurements on angles for head rotation from left/right to right/left is substantially the same with the process for the device for measuring cervical vertebra movement to make measurements on angles for head-up and head-down, head flat turn from left/right to right/left, and the difference only lies in when determining movement angles of the head of the user, the determination unit inquires a mapping table corresponding to head rotation from left/right to right/left in the storage unit based on the distance changes to determine angles for head rotation from left/right to right/left.

Furthermore, in the embodiments of the disclosure, the transmission part and the reception part may be dislocated in the direction of the reference axis, that is, a connection line connecting the transmission part with the reception part is not parallel with, but has an angle being not equal to zero to the reference axis. The reference axis is a central axis of the user's body in a vertical direction when the user stands upright and looks straight ahead. Such a setting manner contributes to determinations of an angle and a direction during head flat turn from left/right to right/left. Specifically, if the transmission part and the reception part are not dislocated in the direction of the reference axis, namely, a connection line connecting the transmission part with the reception part is parallel with the reference axis, at this time, the head flat turn to the left and to the right by the same angle correspond to the same change in a distance between the reception part and the transmission part. That is, even if a movement angle of the head is determined, a direction of movement of the head cannot be determined. In the case that the transmission part and the reception part are dislocated in space, the head flat turn to the left and to the right by the same angle correspond to different changes in a distance between the reception part and the transmission part, so the direction of movement of the head can be simply determined.

Figure 3:
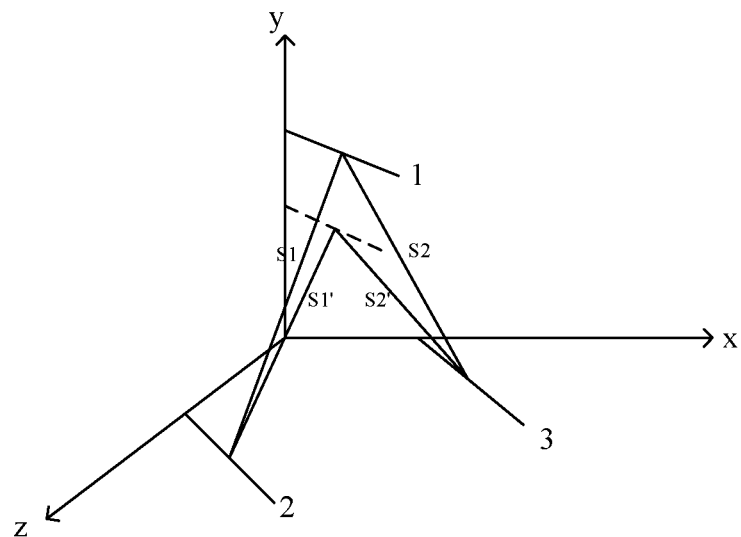
FIG. 3 is a schematic diagram illustrating measurements by the device for measuring cervical vertebra movement on the user's head-up and head-down according to the embodiment shown by FIG. 1.

FIG. 3 is a schematic diagram illustrating measurements by the device for measuring cervical vertebra movement on the user's head-up and head-down according to the embodiment shown by FIG. 1. As shown by FIG. 3, the sensor unit comprises one transmission part 1 and two reception parts 2 and 3. The transmission part 1 has one transmission terminal, and the reception parts 2, 3 each have a reception terminal.

The process for the device for measuring cervical vertebra movement to make measurements on angles for head-up and head-down according to this embodiment is similar with that according to the embodiment shown by FIG. 2. The difference lies in that there are two reception parts in the embodiment shown by FIG. 3. That is, detection signals transmitted by the transmission terminal of the one transmission part 1 are respectively received by the reception terminals of the two reception parts (i.e., the first reception part 2 and the second reception part 3). At this time, the mapping table stored in the storage unit indicates relation between the changes in distances from the one transmission terminal to the two reception terminals and the angle of movement of the head.

As shown by FIG. 3, at the initial state, the distance between the transmission terminal of the transmission part 1 and the reception terminal of the first reception part 2 is S1, and the distance between the transmission terminal of the transmission part 1 and the reception terminal of the second reception part 3 is S2. When the user heads up, the distance between the transmission terminal of the transmission part 1 and the reception terminal of the first reception part 2 is S1', and the distance between the transmission terminal of the transmission part 1 and the reception terminal of the second reception part 3 is S2'. The computation unit may compute a value of S1–S1' and a value of S2–S2'. According to the two values, the determination unit inquires the angle corresponding to the two values in the mapping table. It should be understandable that measurement during head-down is similar with measurement during head-up, and details will not be described here.

In this embodiment, a process for the device for measuring cervical vertebra movement to make measurements on angles for head flat turn from left/right to right/left is substantially the same with the process for the device for measuring cervical vertebra movement to make measurements on angles for head-up and head-down, and the difference only lies in when determining movement angles of the head of the user, the determination unit inquires a mapping table corresponding to head flat turn from left/right to right/left in the storage unit based on the distance changes to determine angles for head flat turn from left/right to right/left.

In this embodiment, a process for the device for measuring cervical vertebra movement to make measurements on angles for head rotation from left/right to right/left is substantially the same with the process for the device for measuring cervical vertebra movement to make measurements on angles for head-up and head-down, head flat turn from left/right to right/left, and the difference only lies in when determining movement angles of the head of the user, the determination unit inquires a mapping table corresponding to head rotation from left/right to right/left in the storage unit based on the distance changes to determine angles for head rotation from left/right to right/left.

Similarly, a measurement method of using three or more reception parts is similar with the process above, and details will not be described here. Using more reception parts may enable more accurate measurements on angles of cervical vertebra movement in different movement patterns.

Furthermore, in the embodiments of the disclosure, the sensor unit may comprise a plurality of transmission parts and one reception part, for example, the number of transmission parts is two or three. The mapping table in the storage unit indicates relations between changes in a distance from each transmission terminal of the transmission parts to the reception terminal of the reception part before and after the head of the user moves and angles of movement of the head. The measuring method of a plurality of transmission parts corresponding to one reception part is similar with the method of one transmission part corresponding to a plurality of reception parts, so details will not be described here.

Figure 4:
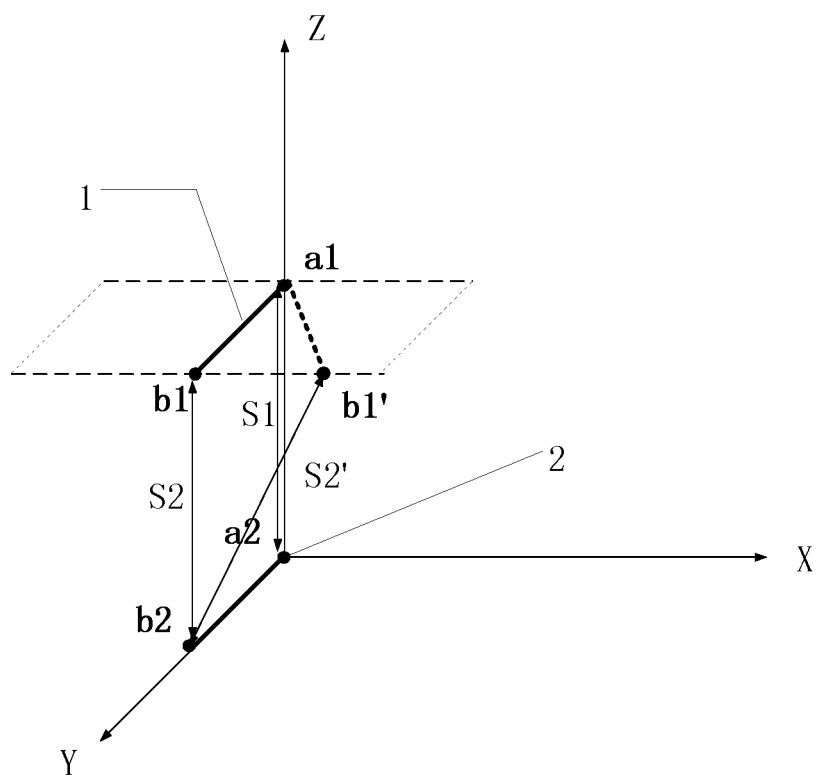
FIG. 4 is a schematic diagram illustrating a device for measuring cervical vertebra movement and its measurement on the user's head flat turn from left/right to right/left according to a third embodiment of the disclosure.

FIG. 4 is a schematic diagram illustrating a device for measuring cervical vertebra movement and its measurement on the user's head flat turn from left/right to right/left according to a third embodiment of the disclosure.

In the device for measuring cervical vertebra movement of the embodiment, the sensor unit comprises one transmission part 1 and one reception part 2. The transmission part 1 has a first transmission terminal a1 and a second transmission terminal b1, and the reception part 2 has a first reception terminal a2 and a second reception terminal b2. The first reception terminal a2 is for receiving detection signals transmitted by the first transmission terminal a1, and the second reception terminal b2 is for receiving detection signals transmitted by the second transmission terminal b1. In order that the detection signals transmitted by the two transmission terminals do not interfere with each other, for example, the detection signals transmitted by the first transmission terminal a1 and the detection signals transmitted by the second transmission terminal b1 are different. For example, different parameters may be used to differentiate detection signals. Parameters of detection signals may be types of the detection signals, such as, laser information, magnetic field information, or may be technical features of the detection signals, such as, wavelength, energy or the like, or other features that can differentiate the detection signals.

The process for the device for measuring cervical vertebra movement to make measurements on head-up and head-down in the embodiment is described below. When cervical vertebra of the user does not move, i.e., the head maintains to be at a fixed position, the distance from the first transmission terminal a1 of the transmission part 1 to the first reception terminal a2 of the reception part 2 of the sensor unit is also fixed, and is recorded as S1. The distance from the second transmission terminal b1 to the second reception terminal b2 is also fixed, and is recorded as S2. Once the head of the user moves, the distance S1' from the first transmission terminal a1 of the transmission part 1 to the first reception terminal a2 of the reception part 2 of the sensor unit and the distance S2' from the second transmission terminal b1 to the second reception terminal b2 vary relative to S1 and S2, respectively. Specifically, when the user heads up, the transmission part 1 moves downward relative to its initial state, at this time, S1' and S2' decrease relative to S1 and S2, respectively. When the user heads down, the transmission part 1 moves upward relative to its initial state, at this time, S1' and S2' increase relative to S1 and S2. Based on information of the detection signals received by the reception part 2, the computation unit may compute the distance S1' from the first transmission terminal a1 to the first reception terminal a2 and the distance S2' from the second transmission terminal b1 to the second reception terminal b2, and further compute the change S1–S1' in a distance from the first transmission terminal a1 to the first reception terminal a2 and the change S2–S2' in a distance from the second transmission terminal b1 to the second reception terminal b2. Lastly, the determination unit may determine a movement angle of the head of the user based on the relation, described in the mapping table stored in the storage unit, between a change in a distance from the first transmission terminal a1 to the first reception terminal a2 and a change in a distance from the second transmission terminal b1 to the second reception terminal b2, and an angle of movement of the head of the user.

In this embodiment, a process for the device for measuring cervical vertebra movement to make measurements on angles for head flat turn from left/right to right/left is substantially the same with the process for the device for measuring cervical vertebra movement to make measurements on angles for head-up and head-down, and the difference only lies in when determining movement angles of the head of the user, the determination unit inquires a mapping table corresponding to head flat turn from left/right to right/left in the storage unit based on the distance changes to determine angles for head flat turn from left/right to right/left.

Specifically, as shown by FIG. 4, when the head of the user flat turns from left/right to right/left, the first transmission terminal a1 of the transmission part 1 is fixed relative to the head of the user. The distance from the first transmission terminal a1 to the first reception terminal a2 does not vary, and is still S1. The distance S2 from the second transmission terminal b1 to the second reception terminal b2 turns to S2'. The computation unit may compute a change S2–S2' in a distance from the second transmission terminal b1 to the second reception terminal b2. Then, the determination unit may determine a movement angle of the head of the user based on the relation, described in the mapping table stored in the storage unit, between a change in a distance from the first transmission terminal a1 to the first reception terminal a2 and a change in a distance from the second transmission terminal b1 to the second reception terminal b2, and an angle of movement of the head of the user.

In this embodiment, a process for the device for measuring cervical vertebra movement to make measurements on angles for head rotation from left/right to right/left is substantially the same with the process for the device for measuring cervical vertebra movement to make measurements on angles for head-up and head-down, head flat turn from left/right to right/left, and the difference only lies in when determining movement angles of the head of the user, the determination unit inquires a mapping table corresponding to head rotation from left/right to right/left in the storage unit based on the distance changes to determine angles for head rotation from left/right to right/left.

The embodiment of the disclosure uses two transmission terminals and two reception terminals, and this may determine a movement angle of the user more accurately and is also good for determining a movement pattern for the head of the user.

Figure 5:
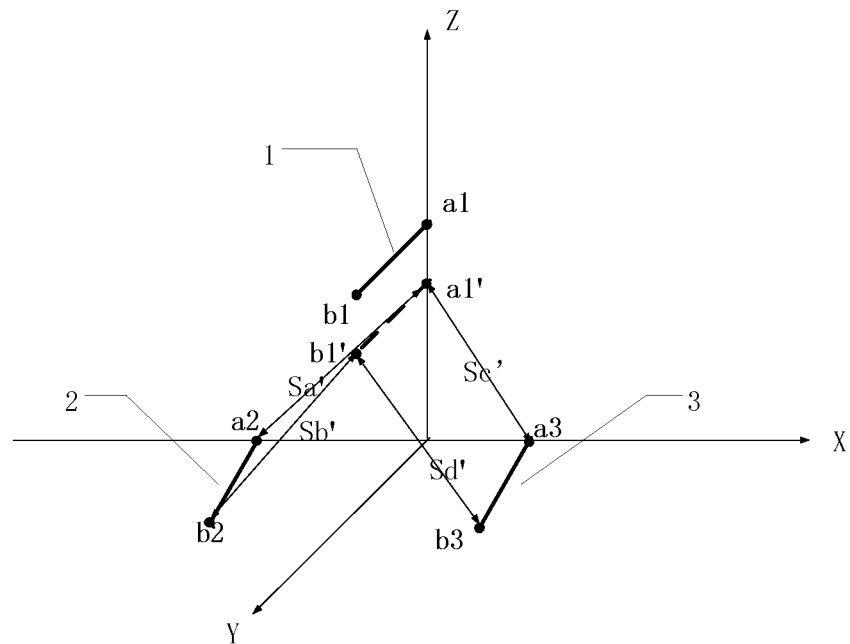
FIG. 5 is a schematic diagram illustrating a device for measuring cervical vertebra movement and its measurements on the user's head-up and head-down according to a fourth embodiment of the disclosure.

FIG. 5 is a schematic diagram illustrating a device for measuring cervical vertebra movement and its measurements on the user's head-up and head-down according to a fourth embodiment of the disclosure.

In the device for measuring cervical vertebra movement of the embodiment, the sensor unit comprises one transmission part and a plurality of reception parts, such as, two or three reception parts. The transmission part has two transmission terminals, and the reception part has two reception terminals.

The following description is made by taking the sensor unit having one transmission part 1 and two reception parts (a first reception part 2 and a second reception part 3, respectively) for instance.

The process for the device for measuring cervical vertebra movement to make measurements on head-up and head-down in the embodiment is described below.

When cervical vertebra of the user does not move, i.e., the head maintains to be at a fixed position, the distances from the first transmission terminal a1 of the transmission part 1 to the first reception terminal a2 of the first reception part 2 and to the first reception terminal a3 of the second reception part 3 of the sensor unit are also fixed, and are recorded as Sa, Sc, respectively. The distances from the second transmission terminal b1 to the second reception terminal b2 of the first reception part 2 and to the second reception terminal b3 of the second reception part 3 are also fixed, and are recorded as Sb and Sd. Once the head of the user moves, the distances Sa', Sc' from the first transmission terminal a1 of the transmission part 1 to the first reception terminal a2 of the first reception part 2 and to the first reception terminal a3 of the second reception part 3 of the sensor unit vary relative to Sa and Sc, and the distances Sb', Sd' from the second transmission terminal b1 to the second reception terminal b2 of the first reception part 2 and to the second reception terminal b3 of the second reception part 3 vary relative to Sb and Sd. For example, when the user heads up, the transmission part 1 moves downward relative to its initial state, at this time, Sa' and Sc' decrease relative to Sa and Sc, and Sb' and Sd' decrease relative to Sb and Sd. When the user heads down, the transmission part 1 moves upward relative to its initial state, at this time, Sa' and Sc' increase relative to Sa and Sc, and Sb' and Sd' increase relative to Sb and Sd. Based on information of the detection signals received by the reception parts, the computation unit may compute the distances Sa', Sc', Sb', Sd' from the two transmission terminals a1, b1 of the first transmission part 1 to the two reception terminals a2 and b2 of the first reception part 2 and to the two reception terminals a3 and b3 of the second reception part 3, respectively, and further compute changes Sa–Sa', Sb–Sb', Sc–Sc', Sd–Sd' in distances from the transmission terminals to the reception terminals before and after the head of the user moves. The storage unit is stored with a mapping table indicating relations between changes in distances from each transmission terminal to the corresponding reception terminal and angles of movement of the head of the user. The determination unit may determine a movement angle of the head of the user based on data in the mapping table.

In this embodiment, a process for the device for measuring cervical vertebra movement to make measurements on angles for head flat turn from left/right to right/left is substantially the same with the process for the device for measuring cervical vertebra movement to make measurements on angles for head-up and head-down, and the difference only lies in when determining movement angles of the head of the user, the determination unit inquires a mapping table corresponding to head flat turn from left/right to right/left in the storage unit based on the distance changes to determine angles for head flat turn from left/right to right/left.

Figure 6:
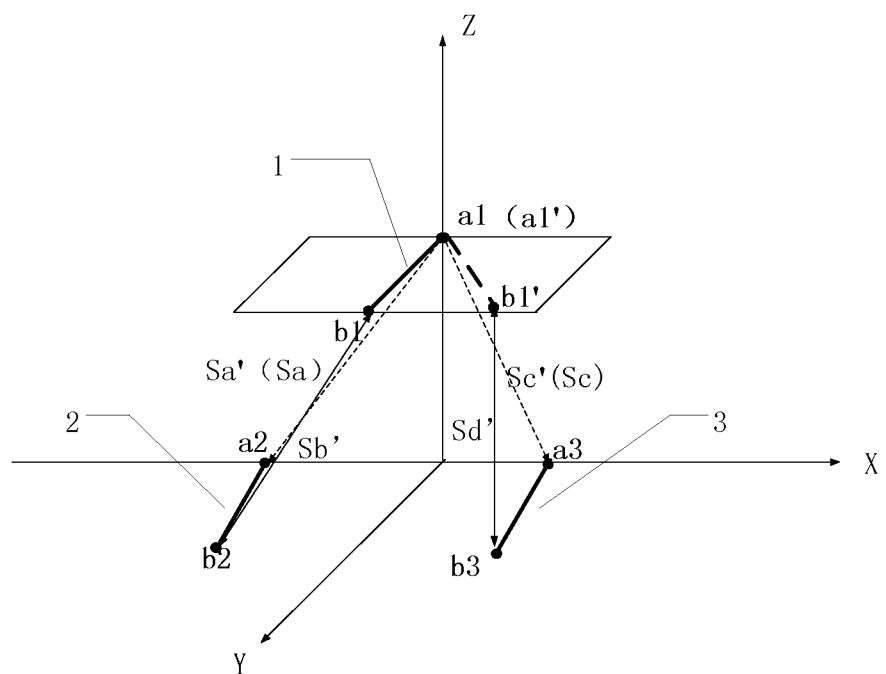
FIG. 6 is a schematic diagram illustrating measurement by the device for measuring cervical vertebra movement on the user's head flat turn from left/right to right/left according to the embodiment shown by FIG. 5.

FIG. 6 is a schematic diagram illustrating measurement by the device for measuring cervical vertebra movement on the user's head flat turn from left/right to right/left according to the embodiment shown by FIG. 5.

As shown by FIG. 6, when the head of the user flat turns to the left, the distances from the first transmission terminal a1 of the transmission part 1 to the first reception terminal a2 of the reception part 2 and to the first reception terminal a3 of the second reception part 3 do not vary, i.e., Sa=Sa', Sc=Sc' as shown in the figure. The distance Sb from the second transmission terminal b1 of the transmission part 1 to the second reception terminal b2 of the first reception part 2 turns to Sb', and the distance Sd from the second transmission terminal b1 of the transmission part 1 to the second reception terminal b3 of the second reception part 3 turns to Sd'. The computation unit may compute changes Sa–Sa', Sb–Sb', Sc–Sc', Sd–Sd' in distances from the transmission part 1 to the reception parts 2 and 3. The storage unit is stored with a mapping table indicating relations between changes in distances from each transmission terminal to the corresponding reception terminal and angles of movement of the head of the user. Lastly, the determination unit may find an angle for movement of the head of the user based on the data in the mapping table.

In this embodiment, a process for the device for measuring cervical vertebra movement to make measurements on angles for head rotation from left/right to right/left is substantially the same with the process for the device for measuring cervical vertebra movement to make measurements on angles for head-up and head-down, and the difference only lies in when determining movement angles of the head of the user, the determination unit inquires a mapping table corresponding to head rotation from left/right to right/left in the storage unit based on the distance changes to determine angles for head rotation from left/right to right/left.

Figure 7:
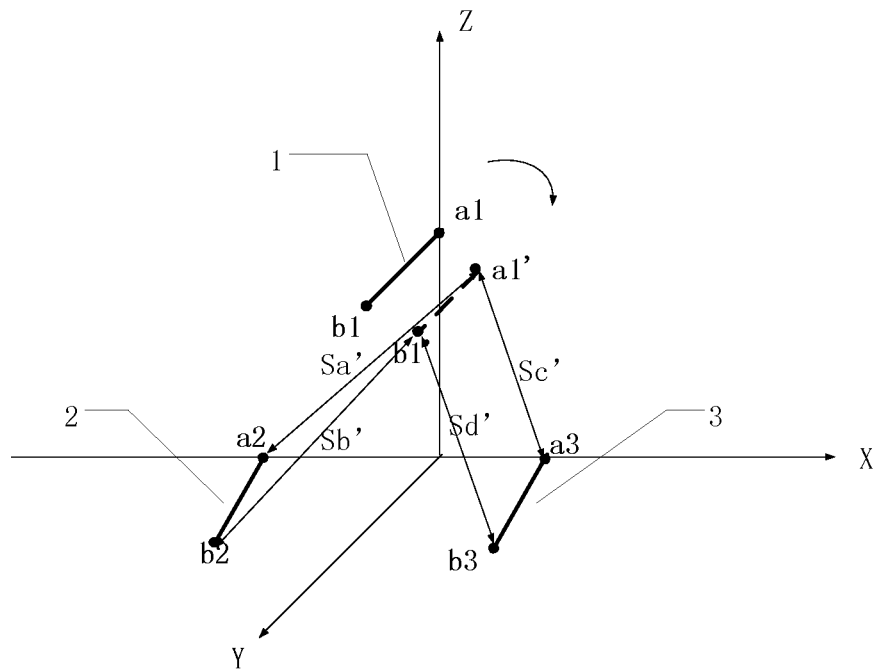
FIG. 7 is a schematic diagram illustrating measurement by the device for measuring cervical vertebra movement on the user's head rotation from left/right to right/left according to the embodiment shown by FIG. 5.

FIG. 7 is a schematic diagram illustrating measurement by the device for measuring cervical vertebra movement on the user's head rotation from left/right to right/left according to the embodiment shown by FIG. 5.

As shown by FIG. 7, when the head turns in the direction indicated by the figure, the distances Sa', Sc' from the first transmission terminal a1 to the first reception terminal a2 of the first reception part 2 and to the first reception terminal a3 of the second reception part 3 of the sensor unit vary relative to Sa and Sc, and the distances Sb', Sd' from the second transmission terminal b1 to the second reception terminal b2 of the first reception part 2 and to the second reception terminal b3 of the second reception part 3 vary relative to Sb and Sd. The computation unit may compute changes Sa–Sa', Sb–Sb', Sc–Sc', Sd–Sd' in distances from the transmission terminals of the transmission part 1 to the reception terminals of the reception parts 2 and 3. The storage unit is stored with a mapping table indicating relations between changes in distances from each transmission terminal to the corresponding reception terminal and angles of movement of the head of the user. The determination unit may find a movement angle of the head of the user based on data in the mapping table.

In the embodiments of the disclosure, the device for measuring cervical vertebra movement may further comprise a movement pattern determination unit configured to determine a movement pattern for the head of the user based on the distance changes and a pre-established relation between the distance changes and movement patterns of the head of the user.

Specifically, taking FIGS. 5-7 for instance, the movement pattern determination unit determines a movement pattern for the head of the user based on changes in distances from the first transmission terminal to the first reception terminals, and changes in distances from the second transmission terminal to the second reception terminals. The computation unit may compute changes Sa–Sa', Sc–Sc' in distances from the first transmission terminal a1 (a') to the first reception terminals a2, a3. For the sake of explanations, Sa–Sa', Sc–Sc' are uniformly termed as $\Delta_1$. The computation unit may compute changes Sb–Sb', Sd–Sd' in distances from the second transmission terminal b1 (b1') to the second reception terminals b2, b3. For the sake of explanations, Sb–Sb', Sd–Sd' are uniformly termed as $\Delta_2$. When change trends of the two are the same, i.e., both $\Delta_1$ and $\Delta_2$ increase or decrease, it can be determined that the movement pattern is head-up or head-down. When the computation unit computes that there is no change in distances from the first transmission terminal a1 (a1') to the first reception terminals a2, a3, i.e., $\Delta_1$ is zero, and there are changes in distances from the second transmission terminal b1 (b1') to the second reception terminals b2, b3, i.e., $\Delta_2$ is not zero, at this time, the movement pattern can be determined as flat turn from left/right to right/left. When the computation unit computes that a trend of changes in distances from the first transmission terminal a1 (a1') to the first reception terminals a2, a3 and a trend of changes in distances from the second transmission terminal b1 (b1') to the second reception terminals b2, b3 are different, i.e., $\Delta_1$ increases but $\Delta_2$ decreases, this movement pattern can be determined as rotation from left/right to right/left.

In needs to be explained that the embodiment is described by taking one transmission part and two reception parts for instance, however, as long as either the transmission part or the reception part include more than two transmission terminals or reception terminals, a determination on a movement pattern for the head of the user can be made effectively. Therefore, this embodiment does not set limitations on the number of transmission parts and the number of reception parts.

Figure 8:
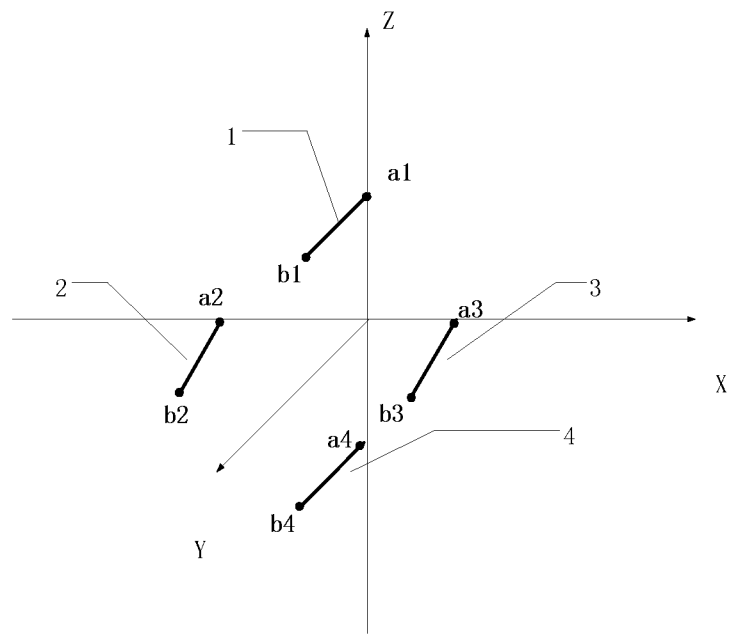
FIG. 8 is a schematic structural diagram illustrating a device for measuring cervical vertebra movement according to a fifth embodiment of the disclosure.

FIG. 8 is a schematic structural diagram illustrating a device for measuring cervical vertebra movement according to a fifth embodiment of the disclosure.

The device for measuring cervical vertebra movement in the embodiment may have more reception parts, for example, as shown by FIG. 8, one transmission part 1 corresponds to three reception parts 2, 3 and 4. In this case, it is only necessary to adjust data in the mapping table accordingly. The process for determining a movement pattern and the process for computing a movement angle are the same with those in the embodiments above.

Furthermore, in the embodiments of the disclosure, the transmission part and the reception part may be cylindrical in shape. In this case, the transmission part and the reception part may be called sensing cylinders. For example, the transmission terminal and the reception terminal may be arranged at or close to the terminals of sensing cylinders, referring to points a1, b1, a2, b2 shown by FIGS. 4-8, which can better indicate angles of movement of the head of the user (i.e., cervical vertebra movement). Furthermore, for example, the transmission part and the reception part have a length of 2~3 cm, and such a range of length may improve measurement accuracy. For example, the transmission part and the reception part may be sensing cylinders cleaved to human bodies or collars worn on the necks, as long as normal transmission and reception of detection signals between the transmission part and the reception part can be achieved.

Figure 9:
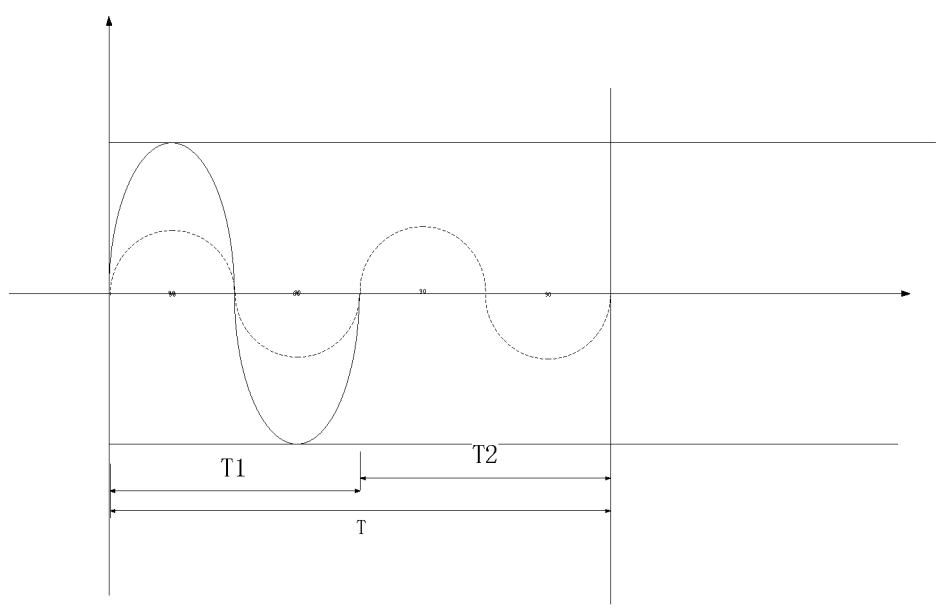
FIG. 9 is a schematic diagram illustrating detection signals transmitted by the transmission part of the device for measuring cervical vertebra movement according to embodiments of the disclosure.

FIG. 9 is a schematic diagram illustrating detection signals transmitted by the transmission part of the device for measuring cervical vertebra movement according to embodiments of the disclosure.

In the embodiments of the disclosure, the transmission part may be an infrared transmitter and the reception part may be an infrared receiver. As shown by FIG. 9, the transmission part periodically transmits detection signals at an interval of T2, and a duration for transmitting detection signals is T1, T2=KT1, wherein K is an integer which is greater than or equal to 1. Infrared rays of the detection signals transmitted by the transmission part may have a wavelength of 5.6~15 μm. The computation unit may compute parameters of the detection signals actually transmitted by the transmission part based on the duration T1 and the interval T2 for the transmission part to transmit detection signals.

When the device for measuring cervical vertebra movement is used for measurement, the computation unit may compute parameters of the detection signals actually transmitted by the transmission part based on the duration T1 and the interval T2 for the transmission part to transmit detection signals, so as to filter detection signals transmitted by the body of the user, making the measurement method more accurate. Specifically, the computation unit may filter waveforms at T2 by deducting a data value obtained at T2 (which may be an energy value or an electrical signal value) from a data value obtained at T1, so as to obtain waveforms actually transmitted by an infrared transmission module within T1, i.e., the oscillogram indicated by full lines. Additionally, far-infrared rays having a wavelength of 5.6~15 μm overlap with waves transmitted by human bodies (an average temperature of human bodies is 36.5° C., accordingly, the wavelength is about 9.4 μm), and frequency bands thereof are in the same range, so far-infrared rays having a wavelength of 5.6~15 μm may make molecular cells within human bodies active and function to activate cells, promote blood circulation, accelerate metabolism and improve immunity of human bodies. Thus, using far-infrared rays having a wavelength of 5.6~15 μm bring no harms but beneficial effects to human bodies. As a result, the user can both gain benefits to his body from infrared rays transmitted by the transmission part in the embodiment, and avoid interferences caused by infrared rays transmitted by his body, so as to ensure measurement accuracy.

The device and method for measuring cervical vertebra movement provided in the embodiments of the disclosure can enable the user to obtain a movement pattern for the head (cervical vertebra) of the user and a movement angle more conveniently and accurately, so as to better monitor movements of his/her own cervical vertebra.

It is understandable that the aforesaid embodiments are only exemplary embodiments for illustrating the principle of the disclosure. Indeed, the disclosure is not limited to this. Without diverging from spirit and essence of the disclosure, those skilled in the art may make various modifications and improvements to the disclosure, which, however, should be also deemed to fall within the protection scope claimed by the disclosure.

The invention claimed is:

1. A device for measuring cervical vertebra movement, the device comprising a sensor unit, a processor and memory,
wherein the sensor unit comprises at least one cylindrically-shaped transmission part and at least one cylindrically-shaped reception part, one of the transmission part and the reception part is arranged to move along with a head of a user, and the other one is arranged to be fixed relative to a body of the user below the user's head,
wherein the transmission part is configured to transmit a plurality of detection signals,
wherein the reception part is configured to receive the plurality of detection signals transmitted by the transmission part,
wherein the processor is configured to compute, based on the plurality of detection signals received by the reception part, a change in a distance between the transmission part and the reception part,
wherein the memory is configured to store a mapping table indicating a relation between the change in the distance and a movement angle of the head of the user,
wherein the processor is configured to inquire the mapping table based on the change in the distance to determine the movement angle of the head of the user,
wherein the cylindrically-shaped transmission part includes two transmission terminals and the cylindrically-shaped reception part includes two reception terminals corresponding to the two transmission terminals, and
wherein the transmission terminals are each configured to transmit one of the plurality of detection signals, and the reception terminals are each configured to receive the detection signal transmitted by its corresponding transmission terminal.

2. The device for measuring cervical vertebra movement according to claim 1, wherein the processor is configured to compute a change in a distance between each transmission terminal and each corresponding reception terminal before and after the head of the user moves.

3. The device for measuring cervical vertebra movement according to claim 1, wherein each transmission terminal transmits a different detection signal.

4. The device for measuring cervical vertebra movement according to claim 1, wherein an angle between a connection line connecting the transmission part with the corresponding reception part and a reference axis is not equal to zero, and wherein the reference axis is a central axis of the body of the user in a vertical direction when the user stands upright and looks straight ahead.

5. The device for measuring cervical vertebra movement according to claim 1, wherein the processor is configured to determine a movement pattern for the head of the user based on the change in the distance and a pre-established relation between the change in the distance and the movement pattern for the head of the user.

6. The device for measuring cervical vertebra movement according to claim 1, wherein the transmission part is an infrared transmitter and the reception part is an infrared receiver.

7. The device for measuring cervical vertebra movement according to claim 6, wherein the detection signal is an infrared ray with a wavelength of 5.6~15 μm.

8. The device for measuring cervical vertebra movement according to claim 1, wherein each of the transmission part and the reception part has a length of 2~3 cm.

9. The device for measuring cervical vertebra movement according to claim 1, wherein the transmission part periodically transmits the plurality of detection signals at an interval of T2, wherein a duration for transmitting the plurality of detection signals is T1, wherein T2=KT1, and wherein K is an integer which is greater than or equal to 1.

10. A method for measuring cervical vertebra movement, the method comprising:
computing, in response to at least one cylindrically-shaped reception part of a sensor unit receiving a plurality of detection signals transmitted by at least one cylindrically-shaped transmission part of the sensor unit, a change in a distance between each transmission part and corresponding reception part before and after a head of a user moves, and
determining a movement angle of the head of the user based on the change in the distance and a pre-established relation between the change in the distance and the movement angle of the head of the user,
wherein one of the transmission part and the reception part is arranged to move along with the head of the user, and the other one is arranged to be fixed relative to a body of the user below the user's head,
wherein the transmission part includes two transmission terminals and the reception part includes two reception terminals corresponding to the two transmission terminals, the transmission terminals are each configured to transmit one of the plurality of detection signals and the reception terminals are each configured to receive the detection signal transmitted by its corresponding transmission terminal, and wherein the step of computing the change in the distance comprises computing the change in the distance between each transmission terminal and each corresponding reception terminal before and after the head of the user moves.

11. The method for measuring cervical vertebra movement according to claim 10, wherein each of the two transmission terminals transmits a different detection signal.

12. The method for measuring cervical vertebra movement according to claim 10, further comprising determining a movement pattern for the head of the user based on the change in the distance and a pre-established relation between the change in the distance and the movement pattern for the head of the user.

13. The method for measuring cervical vertebra movement according to claim 10, wherein the transmission part periodically transmits the plurality of detection signals at an interval of T2, wherein a duration for transmitting the plurality of detection signals is T1, wherein T2=KT1, and wherein K is an integer which is greater than or equal to 1.

14. The device for measuring cervical vertebra movement according to claim 3, wherein the processor is configured to compute a change in a distance between each transmission terminal and each corresponding reception terminal before and after the head of the user moves.

* * * * *